United States Patent [19]

Peyman et al.

[11] Patent Number: 5,510,504

[45] Date of Patent: Apr. 23, 1996

[54] PROCESS FOR THE PREPARATION OF DERIVATIVES OF BIS(AMINO-METHYL) PHOSPHINIC ACID

[75] Inventors: Anuschirwan Peyman; Karl-Heinz Budt, both of Kelkheim; Jörg Spanig, Berlin, all of Germany; Jian-Qi Li, Shanghai, China; Bernd Stowasser, Rüsselsheim, Germany

[73] Assignee: Hoechst Aktiengesellschaft, Frankfurt Am Main, Germany

[21] Appl. No.: 313,044

[22] PCT Filed: Apr. 5, 1993

[86] PCT No.: PCT/EP93/00838

§ 371 Date: Jan. 4, 1995

§ 102(e) Date: Jan. 4, 1995

[87] PCT Pub. No.: WO93/20086

PCT Pub. Date: Oct. 14, 1993

[30] Foreign Application Priority Data

Apr. 6, 1992 [DE] Germany .......................... 42 11 536.1

[51] Int. Cl.⁶ .................................. C07F 9/32; C07F 9/30
[52] U.S. Cl. ............................. 558/145; 558/166; 562/16
[58] Field of Search ........................ 558/145, 131, 558/166; 562/16

[56] References Cited

U.S. PATENT DOCUMENTS 4,171,969 10/1979 Maier .......................................... 71/86

FOREIGN PATENT DOCUMENTS 2380289 2/1978 France .
3824961A1 7/1981 Germany .

OTHER PUBLICATIONS

Peyman et al., "C2–Symetric Phosphinic Acid Inhibitors of HIV Protease," Tetrahedron Letters, vol. 33, No. 32, pp. 4549–4552, 1992.

Tyka et al., "Synthese Symmetrischer Und Asymmetrischer a, a'-Bis(aminoalkyl)—Phoshinsäuren Des Typs NH2CHR1 (NH2CHR2) PH (O) OH (R1=Ph; R2=Ph, Me)," Phosphorus, Sulfur, and Silicon, vol. 62, pp. 75–81, 1991.

Derwent Abstract of DE 3824961A1, 1995.

*Primary Examiner*—Johann Richter
*Assistant Examiner*—Michael G. Ambrose
*Attorney, Agent, or Firm*—Finnegan, Henderson, Farabow, Garrett & Dunner

[57] ABSTRACT

A process for the preparation of $\alpha$- or $\alpha,\alpha'$-substituted derivatives of the bis(aminomethyl)phosphinic acid of the formula I and their acid or basic salts,

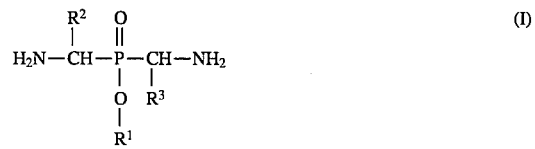

in which $R^1$, $R^2$ and $R^3$ are defined as in the description, wherein a bis(aminomethyl)phosphinate is converted into the corresponding bisimine, which is alkylated by $R^2$ and $R^3$ in the $\alpha$- and/or $\alpha,\alpha'$-position after reaction with a base, and is converted into a compound of the formula I by subsequent treatment with an acid.

7 Claims, No Drawings

PROCESS FOR THE PREPARATION OF DERIVATIVES OF BIS(AMINO-METHYL) PHOSPHINIC ACID

This application is a continuation of International Application No. PCT/EP93/00838, filed Apr. 5, 1993.

α-Aminophosphonic acids and their derivatives are becoming increasingly important, often as enzyme inhibitors, in biochemistry, pharmaceutical chemistry and in the area of crop protection [E. Neuzil, A. Cassaigne, Exp. Ann. Biochim. Medicale 34 (1980) 165]. There is a whole range of processes for preparing this class of compound and these are summarized in various articles [Kukhar and Solodenko, Russ. Chem. Rev. 56 (1987) 859; Redmoore, Topics in Phosphorus Chemistry, vol. 11, Grayson and Griffith, Ed., Wiley, 1976, 515].

The preparation of another class of compounds, bis(aminomethyl)phosphinic acid and its derivatives, which are also gaining in importance in pharmaceutical chemistry (EP 0435 059 A1), is far more complex and not very well documented. The synthesis of the parent compound was first described by Meier [L. Meier, J. Organomet. Chem. 178 (1979) 157; DE 2805074A1, see also Kober et al., DE 3824961A1]. A possibility for preparing α- or α,α'-substituted derivatives of bis(aminomethyl)phosphinic acid is described by Tyka et al. [Phosphorus, Sulfur and Silicon 62 (1991) 75]. The method is based on the addition reaction of hypophosphorous acid with Schiff's bases to form aminoalkylphosphonous acids in the first step and the reaction of the latter with arylidenebisamides to give α,α'-bis(aminoalkyl)phosphinic acids. This process, however, is restricted to reaction with arylidenebisamides and is further distinguished by modest yields. Only modest yields were observed also for the double addition reaction of hypophosphorous acid with Schiff's bases to form α,α'-bis(aminoalkyl)phosphinic acids.

The invention relates to a new process for the preparation of α- or α,α'-substituted derivatives of the bis(aminomethyl)phosphinic acid of the formula I and their acid or basic salts,

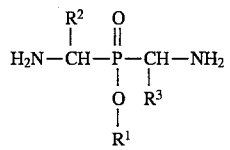

in which $R^1$ is $R^6$=alkyl, $C_2$–$C_{18}$ alkenyl, $C_2$–$C_{18}$ alkynyl, $C_6$–$C_{12}$ aryl or $C_7$–$C_{20}$ arylalkyl and aryl or arylalkyl may be mono- or polysubstituted by fluorine, chlorine, bromine, $NO_2$, CN, OH, COOH, $C_1$–$C_6$ alkyl, $C_1$–$C_6$ alkoxy, C(O)—O—($C_1$–$C_6$) alkyl, C(O)—($C_1$–$C_6$) alkyl or O—C(O)—($C_1$–$C_6$) alkyl and $R^1$ is also hydrogen or basic salt radicals of α- or α,α'-substituted derivatives of the bis(aminomethyl)phosphinic acid, especially alkali metal or alkaline earth metal salts, or else ammonium or trialkylammonium salts, $R^2$ and $R^3$ are identical or different and are, independently of each other, hydrogen, $C_1$–$C_{18}$ alkyl, $C_2$–$C_{18}$ alkenyl, $C_2$–$C_{18}$ alkynyl, $C_6$–$C_{12}$ aryl or $C_7$–$C_{22}$ arylalkyl, where alkyl, alkenyl or alkynyl may each be mono-or polysubstituted by fluorine, chlorine, bromine, $NO_2$, $NH_2$, CN, OH, COOH, C(O)—O—($C_1$–$C_6$) alkyl, C(O)—($C_1$–$C_6$) alkyl, O—C(O)—($C_1$–$C_6$) alkyl or $C_1$–$C_6$ alkoxy and aryl may be mono- or polysubstituted by fluorine, chlorine, bromine, $NO_2$, CN, OH, COOH, $C_1$–$C_6$ alkyl, $C_1$–$C_6$ alkoxy, C(O)—O—($C_1$–$C_6$) alkyl, C(O)—($C_1$–$C_6$) alkyl or O—C(O)—($C_1$–$C_6$) alkyl, with the proviso that if $R^2$= hydrogen and $R^3$ has the above-mentioned meaning, $R^3$ must not also be hydrogen, and vice versa.

$R^1$ is preferably hydrogen, $C_1$–$C_4$ alkyl, $C_2$–$C_4$ alkenyl, phenyl, benzyl, $Li^+$, $Na^+$, $K^+$, $Mg^{2+}$, $NH_4^+$, $HN(C_2H_5)_3^+$, especially hydrogen and $C_1$–$C_4$ alkyl.

$R^2$ and $R^3$ are particularly preferably $C_1$–$C_4$ alkyl, $C_2$–$C_4$ alkenyl, alkenyl, $C_2$–$C_6$ alkynyl, $C_6$–$C_{12}$ aryl, $C_7$–$C_{13}$ arylalkyl, where aryl or arylalkyl may be mono- or polysubstituted by chlorine, bromine, —CN or O—$C_1$–$C_3$ alkyl.

$R^2$ and $R^3$ are very particularly preferably $C_1$–$C_6$ alkyl, $C_2$–$C_6$ alkenyl, $C_2$–$C_6$ alkynyl and benzyl.

Formula I furthermore encompasses the acid salts of the α- or α,α'-substituted derivatives of bis(aminomethyl)phosphinic acid, especially the hydrochlorides, hydrobromides, hydrogen sulfates, particularly preferably the hydrochlorides and hydrobromides.

A. Synthesis of compounds of the formula II

The process is distinguished in that the amino groups in the bis ( aminomethyl ) phosphinic acid are first protected (formula II) [synthesis by the method of L. Meier, J. Organomet. Chem. 178 (1979) 157].

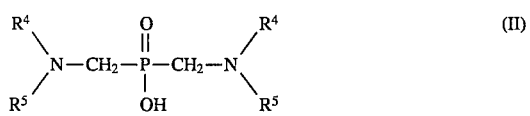

In formula II, $NR^4R^5$ should be the protected amino function. The usual protective groups for amino functions [Greene, Protective Groups in Organic Synthesis, Wiley, 1979] can be inserted as the protective groups $R^4$ and $R^5$ in a known manner, but in particular the protective groups which are known in peptide chemistry [Bodanszky & Bodanszky, The Practice of Peptide Synthesis, Springer, 1984] are introduced in the manner which is generally known for amino acids. The reaction of bis(aminomethyl)phosphinic acid with 2 to 2.5 equivalents of di-tert-butylpyrocarbonate in the presence of a slight excess of base (relative to the amino groups), preferably NaOH in aqueous dioxane at −30° to +50° C. preferably at −10° to +20° C. for 0.5–3 hours, is particularly preferred. Working up takes place in a manner known per se, as described by Bodanszky for amino acids, by evaporation, acidification to pH 2–3 and extraction.

B. Synthesis of compounds of the formula III

The N,N'-protected bis(aminomethyl)phosphinic acid II is converted into a compound of the formula III in the next step, using a compound of the formula $R^6$—OH.

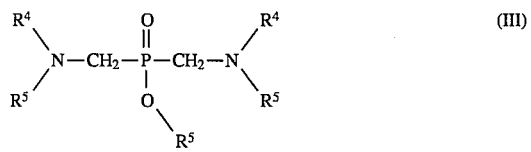

$R^4$ and $R^5$ here are defined as in formula II and $R^6$ has the meaning mentioned under $R^1$.

$R^6$ is preferably $C_1$–$C_4$ alkyl, $C_2$–$C_4$ alkenyl, phenyl, benzyl, very particularly preferably $C_1$–$C_4$ alkyl.

Esterification takes place by reacting the protected phosphinic acid II with the compounds $R^6$—OH ($R^6$ being defined as above) and a suitable coupling reagent. The conditions for esterification correspond to the generally known procedures for esterifying phosphonic acids, as specified, for example, in Houben-Weyl (vol. 12/1 & E2). Alternatively, coupling reagents, as employed for esterifying N-protected α-aminocarboxylic acids [Janin et al. Tetrahedron Lett. 28 (1987) 1661], can be used or coupling reagents which are used in DNA synthesis for the synthesis of triesters of phosphoric acid may also be employed [Sonveaux, Bioorg. Chem. 14 (1986) 274].

The reaction of II with 1–10 equivalents of R⁶—OH and 1–2, preferably 1–1.2 equivalents of dicyclohexylcarbodiimide (DCC) in a suitable organic solvent, preferably THF, at temperatures of 0°–100° C., preferably at 40°–70° C. (at 40°–67° C. in THF) for 0.5 to 48 hours, is particularly preferred. The esters III which are produced are purified in a manner known per se by evaporation, removal by filtration of N,N'-dicyclohexylurea, crystallization and chromatography on silica gel.

Also particularly preferred is the reaction of II with R⁶—OH in the presence of alkyl chloroformates or alkenyl chloroformates which are used to esterify α-aminocarboxylic acids [Janin et al., Tetrahedron Lett. 28 (1987) 1661]. Surprisingly, this method may be transposed to the esterification of the phosphinic acids II. In this case, II is reacted with 1–2 equivalents, preferably 1 to 1.3 equivalents of alkyl or alkenyl chloroformate, preferably isobutyl or isopropenyl chloroformate, in the presence of 1 to 2, preferably 1 to 1.2 equivalents of trialkylamine, preferably triethylamine (TEA) or diisopropylethylamine (DIPEA), and a catalytic amount of dimethylaminopyridine (DMAP), preferably 0.1 equivalent of DMAP, as well as 1–10 equivalents of R⁶—OH in a suitable organic solvent, preferably methylene chloride (CH₂Cl₂), chloroform (CHCl₃), tetrahydrofuran (THF), acetonitrile, dimethylformamide (DMF), dimethyl sulfoxide (DMSO), dioxane, toluene, benzene or ethyl acetate (EA), with CH₂Cl₂ or CHCl₃ and toluene being particularly preferred, at temperatures of −10° to +50° C., preferably 0°–10° C. for 1–12 hours. Working up and purification take place in a manner known per se as described for the esterification of α-amino acids [Janin et al., Tetrahedron Lett. 28 (1987) 1661] by extraction, crystallization and chromatography on silica gel.

The synthesis of compounds III, especially compounds III in which R⁴ is benzyl and R⁵ is hydrogen, may also take place using an alternative process. The relevant parent compound, bis(benzylaminomethyl)phosphinic acid has already been described in the literature, not however, its ester [L. Meier, J. Organomet. Chem. 178 (1979) 157; DE 2805074A1].

These compounds are prepared from bis(chloromethyl)phosphinic chloride, which was also described by Meier [L. Meier, J. Organomet. Chem. 178 (1979) 157; DE 2805074A1]. This is converted to the bis(chloromethyl)phosphinate of the formula IX

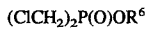

(ClCH₂)₂P(O)OR⁶      (IX)

by reaction with at least one equivalent of R⁶—OH (R⁶—OH defined as above) in a suitable organic solvent, preferably toluene, benzene, CH₂Cl₂, CHCl₃, THF or ether at temperatures from 0° to 100° C., preferably at 10° to 40° C. The reaction may also take place in the presence of one equivalent of a base, preferably a trialkylamine, particularly preferably triethylamine (TEA) or diisopropylethylamine (DIPEA) and also in the presence of a catalytic amount of dimethylaminopyridine (DMAP), preferably 0.1 equivalent of DMAP. If R⁶—OH is a low-boiling alcohol, for example ethanol, then this may itself act as solvent. The esters which are formed are purified in a manner known per se by filtration, evaporation, crystallization and distillation or chromatography on silica gel.

To prepare bis(benzylaminomethyl)phosphinates, an excess above the stoichiometrically required amount of benzylamine is reacted at temperatures of 0° to 110° C. The products are purified in a manner known per se by filtration, evaporation, crystallization and distillation or chromatography on silica gel. The bis(benzylaminomethyl)phosphinate hydrochlorides are preferably isolated.

C. Synthesis of the compounds of the formula IV

In the following step the amino functions of the ester of the formula III are de-protected, bis(aminomethyl)phosphinates of the formula IV or their acid salts being produced.

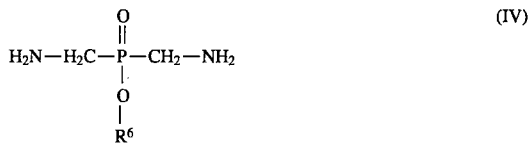

De-protection takes place by processes per se [Greene, Protective Groups in Organic Synthesis, Wiley 1979; Bodanszky & Bodanszky, The Practice of Peptide Synthesis, Springer 1984], depending on the protective group used. For example, the tert-butyloxycarbonyl protective group is removed by treatment with a saturated solution of HCl in dioxane or methanol at 20°–40° C. for 10–30 minutes and subsequent evaporation.

Benzyl protective groups are removed by catalytic hydrogenation (5% Pd/C or PtO₂ or Pt/C) at atmospheric pressure and at 10°–70° C., preferably 20°–40° C. Particularly suitable solvents for this are ethanol, ethanol/glacial acetic acid or glacial acetic acid.

D. Synthesis of compounds of the formula V

The bis(aminomethyl)phosphinate IV which is produced is converted to bis(iminomethyl)phosphinate V in the following step.

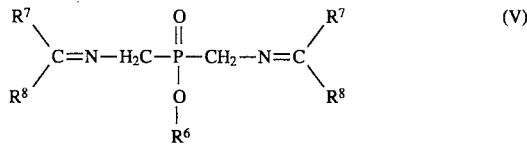

Here, R⁷ and R⁸ are identical or different and are hydrogen, C₁–C₂₀ alkyl, C₂–C₂₀ alkenyl, C₂–C₂₀ alkynyl or C₆–C₁₂ aryl. R⁷ and R⁸ together may also form a ring system, for example a C₅–C₃₀ alkyl ring system, a C₅–C₃₀ alkenyl ring system or a C₉–C₃₀ alkylaryl ring system, where the ring systems may be mono-, di- or tricyclic. In this case, R⁷ and R⁸ are for example the skeletons of cyclopentanone, cyclohexanone, fluorenone, anthrone, camphor, menthone, pulegone, carvone, carone or verbenol.

Preferred compounds V are those in which R⁷ and R⁸ are phenyl/phenyl, phenyl/methyl, phenyl/hydrogen or the camphor skeleton. Particularly preferred are compounds V in which R⁷ and R⁸ are phenyl/phenyl.

a. Synthesis of the bis(iminomethyl)phosphinates V takes place by reacting IV (preferably in the hydrochloride or hydrobromide form) with 2 to 3 equivalents (preferably with 2 to 2.2 equivalents) of the compound VI (R⁷ and R⁸ defined as above)

in a suitable anhydrous organic solvent (preferably CH₂Cl₂, CHCl₃, THF, acetonitrile, dimethylformamide, dimethyl sulfoxide, dioxane, toluene, benzene or ethyl acetate, particularly preferably CH₂Cl₂ and CHCl₃ or toluene and benzene, very particularly preferably CH₂Cl₂ and CHCl₃) at temperatures from 0° to 100° C. (preferably 10°–30° C.) for 1 to 48 hours (preferably 3 to 24 hours). The reaction is preferably performed under an inert gas, for example nitrogen or argon. Working up and purification of compounds V take place by generally conventional methods, that is filtration, extraction, drying, recrystallization and chromatography. For example, after filtration and evaporation of the solution, the residue is taken up once more in a non-polar solvent, preferably ether, filtered again, dried, evaporated and chromatographed on silica gel or recrystallized.

b. Alternatively, the bis(iminomethyl)phosphinates V may be prepared by reacting the bis(aminomethyl)phosphinates IV with 2 to 3 equivalents (preferably 2 to 2.2 equivalents) of compound VII ($R^7$ and $R^8$ defined as above) and a catalytic amount of acid (preferably p-toluenesulfonic acid)

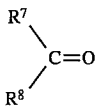   (VII)

in a suitable anhydrous organic solvent (preferably $CH_2Cl_2$, $CHCl_3$, THF, acetonitrile, dimethylformamide, dimethyl sulfoxide, dioxane, toluene or benzene, particularly preferably $CH_2Cl_2$ and $CHCl_3$ or toluene and benzene, very particularly preferably toluene and benzene) at temperatures of from 0° to 120° C. (preferably while boiling) for 1 to 48 hours (preferably 10 to 24 hours) under conditions where water separates out. Conditions which serve to remove water from the reaction mixture are well-known and are preferably a water separator and Soxhlet apparatus with molecular sieve. Working up and purification of the compounds V take place by generally conventional methods of filtration, extraction, drying, recrystallization and chromatography. Preferably purification is achieved by chromatography on silica gel.

E. Synthesis of compounds of the formula VIII

In the next step, the bis(iminomethyl)phosphinates V are alkylated, resulting in α,α'-substituted bis(iminoalkyl)phosphinates VIII.

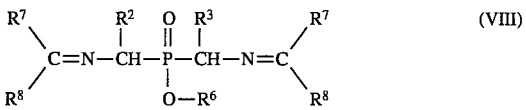   (VIII)

Here, $R^2$, $R^3$ and $R^6$ are defined as in formula I and $R^7$ and $R^8$ as in formula V.

The alkylation can be carried out stereoselectively by employing chiral radicals $R^7$ or $R^8$ or $R^7$ and $R^8$. In this case, $R^7$ and $R^8$ are, by way of example, [+] or [−] camphor, [+] or [−] menthone, [+] or [−] pulegone, [+] or [−] carvone, [+] or [−] verbenol.

$e_1$) To prepare compounds of the formula VIII in which $R^2$ is identical to $R^3$, but is not hydrogen, the bis(iminomethyl)phosphinates V are dissolved in a suitable absolute organic solvent (preferably THF, ether, n-pentane, n-hexane, n-heptane, particularly preferably THF) and are reacted, preferably under inert conditions (particularly preferably under argon) at temperatures of from −90° to +30° C. (preferably −80° to −50° C.), with 2 to 2.2 equivalents of a suitable base, preferably butyllithium, lithium diisopropylamine (LDA), sodium hydride, sodium amide, potassium tert.-butylate or complex bases (sodium amide/$R^{13}$ONa, where $R^{13}$ is $C_2$–$C_6$ alkyl or $CH_3CH_2OCH_2CH_2$) for 5–30 minutes. Afterwards, also preferably at −80° to −50° C., 2 to 5 (preferably 2 to 2.2) equivalents of compound $R^3$—X are added. Here, $R^3$ is defined as in formula I, but is not hydrogen, X is a leaving group, preferably chlorine, bromine, iodine, O-p-toluenesulfonate, O-trifluoromethyl-sulfonate or O-methylsulfonate, particularly preferably chlorine, bromine or iodine. The reaction is stirred for another 2 to 48 hours at −80° to +30° C. (preferably −80° to −40° C.). Well-known methods, such as filtration, extraction, recrystallization and chromatography are used for working up and purifying. For example, the reaction mixture is evaporated, distributed between water and ether, the organic phase dried in a well-known manner and the diastereomeric products chromatographed on silica gel.

$e_2$) To prepare compounds VIII in which $R^2$ is hydrogen and $R^3$ is defined as in formula I, the procedure is as in $e_1$) but using only 1 to 1.2 equivalents of base and 1 to 1.2 equivalents of $R^3$—X. The reaction time is from 5 minutes to 3 hours.

$e_3$) To prepare compounds VIII in which $R^2$ and $R^3$ are defined as in formula I but neither is hydrogen, the compounds of the formula VIII obtained by $e_2$) are reacted with $R^2$—X instead of $R^3$—X under the conditions mentioned in $e_1$), though only 1 to 1.2 equivalents of base and 1 to 1.2 equivalents of $R^2$—X are used. The reaction time is from 10 minutes to 48 hours.

The alkylation of the bis(iminomethyl)phosphinate described in $e_1$) to $e_3$) is particularly preferred.

f. Alternatively, the compounds VIII may also be obtained by phase-transfer catalysis.

$f_1$) To prepare compounds in which $R^2$ and $R^3$ are identical but $R_2$ is not hydrogen, a mixture of V, a catalytic amount of $R^9R^{10}R^{11}R^{12}NZ$, 2 to 3 equivalents (preferably 2 to 2.5 equivalents) of $R^3$—X and 2 to 25 equivalents (preferably 8 to 20 equivalents) of an alkali metal hydroxide or alkaline earth metal hydroxide, especially KOH or NaOH, and a water-immiscible solvent, preferably $CH_2Cl_2$, toluene, benzene, 1,1,2,2-tetrachloroethane, particularly preferably $CH_2Cl_2$ and toluene, is stirred for 1–24 hours at temperatures from 0° to 50° C., preferably 10° to 30° C.

Here, N is either nitrogen or phosphorus, but preferably nitrogen; $R^9$, $R^{10}$, $R^{11}$ and $R^{12}$ are identical or different and independently of each other are $C_1$–$C_{20}$ alkyl, $C_2$–$C_{20}$ alkenyl, $C_2$–$C_{20}$ alkynyl, $C_6$–$C_{12}$ aryl or $C_7$–$C_{20}$ arylalkyl, preferably $C_3$–$C_{16}$ alkyl, particularly preferably n-butyl; Z is an anion of an inorganic salt such as chloride, bromide, iodide or hydrogen sulfate, particularly preferably chloride, bromide and hydrogen sulfate; preferably 0.03 to 0.3, particularly preferably 0.05 to 0.15 equivalent of the catalyst $R^9R^{10}R^{11}R^{12}NZ$ is used. $R^3$—X is defined here as above.

Well-known methods are used for working up and purification, such as filtration, extraction, recrystallization and chromatography. Usually the mixture is filtered, the solvent evaporated, the residue taken up in ether, filtered once again in order to remove the catalyst completely and the product purified by chromatography on silica gel.

$f_2$) To prepare compounds VIII in which $R^2$ is hydrogen and $R^3$ is defined as in formula I, the procedure is as in $f_1$) but using only 2 to 10, preferably 3 to 7, equivalents of the alkali metal hydroxide or alkaline earth metal hydroxide and 1 to 1.2 equivalents of $R^3$—X.

$f_3$) To prepare compounds of formula VIII in which $R^2$ and $R^3$ are defined as in formula I, but neither is hydrogen, the compounds of formula VIII obtained as in $f_2$ are reacted with $R^2$—X instead of $R^3$—X under the conditions mentioned in $f_1$). However, 2 to 10, preferably 3 to 7, equivalents of the alkali metal hydroxide or alkaline earth metal hydroxide and 1 to 1.2 equivalents of $R^2$—X are used.

g) The alkylations using phase-transfer catalysis which are described under $f_1$), $f_2$) and $f_3$) may also be performed without a solvent. In this case, the procedure described there is used, but working without a solvent and with methyltrioctylammonium chloride (for example, Aliquat® 336) instead of $R^9R^{10}R^{11}R^{12}NZ$. Well-known methods such as filtration, extraction, recrystallization and chromatography are used for working up and purifying. The reaction mixture is usually taken up in dichloromethane, the catalyst removed by the addition of silica gel and filtration and the product purified by chromatography on silica gel.

F. Synthesis of compounds of the formula I in which $R^1$ is $R^6$

To synthesize compounds of the formula I in which $R^2$ is $R^6$ VIII in a suitable organic solvent, preferably ether, THF, $CH_2Cl_2$, $CHCl_3$ or dioxane, is reacted with 5–15% strength aqueous HCl or HBr, preferably 10% strength aqueous hydrochloric acid, for 1 to 48 hours, preferably 5 to 24 hours, at temperatures from 0° to 50° C., preferably 10° to 30° C. Well-known methods such as filtration, extraction, recrystallization, freeze-drying and chromatography are used for working up and purifying. Conventionally the phases are separated and the aqueous phase is extracted with a suitable solvent, preferably ether. The aqueous phase is then stirred with solid $K_2CO_3$ and $CH_2Cl_2$ for 5 to 20 minutes and the compound of the formula I is recovered from the organic phase. Chromatography on silica gel may additionally be used for purification. The compound of the formula I may be converted into corresponding salts by ion exchange chromatography or by reaction with acids.

G. Synthesis of compounds of the formula I in which $R^1$ is not $R^6$ $i_1$) To synthesise compounds of the formula I in which $R^1$ is not $R^6$, the compound of the formula VIII or the compound of the formula I in which $R^1$ is $R^6$, in 30% strength HBr or HCl, preferably HBr, is stirred in glacial acetic acid. The reaction is performed at 0°–80° C., preferably at 20°–70° C. The reaction time is 10 to 300 minutes, preferably 10–45 minutes. Afterwards glacial acetic acid and excess HBr are removed by distillation under vacuum. Well-known methods such as filtration, extraction, recrystallization, freeze-drying and chromatography are used for working up and purifying. X may be converted into corresponding salts by ion exchange chromatography or by reaction with acids.

$i_2$) Compounds of the formula I in which $R^1$ is not $R^6$ may be obtained alternatively from compounds of the formula I in which $R^1$ is $R^6$, which depends on the specific properties of the radical $R^1$ (which $R^6$) which is to be eliminated, by well-known methods. Examples which may be cited are the elimination of $R^6$= benzyl by hydrogenation or of $R^6$= methyl or ethyl by reaction with trimethylsilyl bromide or trimethylsilyl iodide in a suitable organic solvent such as for instance dioxane at room temperature.

EXAMPLES

Example 1

Bis (N-tert-butoxycarbonyl-aminomethyl) phosphinic acid (1)

1.0 M aqueous sodium hydroxide solution (37.6 ml; 37.60 mmol) and tert-butoxycarbonyl anhydride (5.69 g; 26.10 mmol) in dioxane (3 ml) are added in succession to a solution of bis(aminomethyl)phosphinic acid hydrochloride (2.00 g; 12.46 mmol) in water (20 ml) and dioxane (20 ml) at 0° C. with stirring. The reaction solution is warmed to room temperature and after one hour is evaporated under reduced pressure to a volume of about 40 ml. The solution is treated with ethyl acetate (40 ml) and acidified to a pH of 2–3 using saturated aqueous $KHSO_4$ solution. The separated aqueous phase is extracted with ethyl acetate (4×50 ml). The combined organic phase is dried over $Na_2SO_4$ and evaporated under reduced pressure. The phosphinic acid 1 is obtained as crude product (3.20 g).

$^1$H NMR ($\delta$/ppm/) (200 MHz $CDCl_3$): 1.48 (18H, s, $CH_3$); 3.53 (4H, bd, J 7.5 Hz, $CH_2$); 5.70 (1H, bs NH); 6.25 (1H, bs, NH);

MS (FAB, NBA, m/e): 325 (M+H$^+$), 269 (M-55), 213 (269- 56) (100%).

Example 2

Ethyl bis(N-tert-butoxycarbonylaminomethyl)phosphinate (2)

DCC (190 mg; 0.92 mmol) in THF (4 ml) is added dropwise over the course of 4 minutes to a solution of the phosphinic acid 1 (270 mg; 0.83 mmol) in dry THF (4 ml) and absolute ethanol (0.30 ml; 5.15 mmol) which is boiling under reflux. After 1.5 hours (check via DC) the reaction solution is cooled to room temperature and filtered. The filtration residue is washed with ether.

The filtrate is extracted with water (2×20 ml). The organic phase is dried over $Na_2SO_4$ and evaporated under reduced pressure. The phosphinate 2 is obtained after purification using column chromatography on silica gel (ethyl acetate/heptane= 3/2) (100 mg, 34% of theory). m.p. 117.5°–120° C.

$^1$H NMR ($\delta$/ppm/)(200MHz, $CDCl_3$): 1.30 (3H, t, J 7 Hz, $CH_2CH_3$); 1.45 (18H, s, $(CH_3)_3C$); 3.23 (2H, dt, J15 and 5Hz, $CH_2$); 3.84 (2H, m, $CH_2$); 4.18 (2H, dq, J 6 and 6 Hz, $OCH_2$); 5.48 (2H, bs, NH);

MS (FAB, NBA, m/e): 353 (M+H+); 297 (M-55); 241 (297- 56)(100%).

Example 3

Ethyl bis(N-tert-butoxycarbonylaminomethyl)phosphinate (2)

Isobutyl chloroformate (1.50 ml; 11.48 mmol) is added dropwise and with stirring to a solution of the phosphinic acid 1 (3.200 g; 9.88 mmol) in a mixture of methylene chloride (50 ml), ethanol (3.00 ml; 51.59 mmol), triethylamine (1.40 ml; 10.06 mmol) and N,N-dimethylaminopyridine (10 mg) at 0° C. After 90 minutes the reaction solution is extracted with saturated aqueous ammonium chloride solution (30 ml) and saturated aqueous $KHCO_3$ solution (30 ml). The organic phase is dried over $Na_2SO_4$ and evaporated under reduced pressure. The phosphinate 2 (700 mg, 20% of theory) is obtained after purification on silica gel, using column chromatography (ethyl acetate/heptane=3/2). Spectroscopic data is given above.

Example 4

Ethyl bis(N-diphenylmethyleneaminomethyl)phosphinate (3)

The tert-butoxycarbonyl protective group is removed from the ethyl phosphinate 2 (100 mg; 0.28 mmol) using 3N methanolic hydrochloric acid (30 ml) (check via DC). The reaction solution is evaporated under reduced pressure. Diphenylmethanimine (0.100 ml; 0.60 mmol) is added dropwise to the suspension of the crude product in methylene chloride (20 ml) under an atmosphere of nitrogen. The reaction solution is filtered after being stirred for 16 hours at room temperature. The filtrate is evaporated under reduced pressure. The crude product is taken up in ether, filtered and extracted with water (2× 20 ml). The organic phase is dried over $Na_2SO_4$ and evaporated under reduced pressure. The diphenylmethylene phosphinate 3 (71 mg, 53% of theory) is obtained after purification on silica gel using column chromatography (ethyl acetate/heptane=1/1).

$^1$H NMR ($\delta$/ppm/)(200MHz, $CDCl_3$): 1.30 (3H, t, J 7 Hz, $CH_3$); 4.10 (2H, d, J 14 Hz, $CH_2N$); 4.14 (4H, m, $OCH_2$); 7.17–7.63 (20H, m, $H_{arom.}$);

MS (FAB, NBA, m/e): 481 (M+H$^+$); 389; 327; 253; 209 (100%).

Example 5

Ethyl (N-diphenylmethyleneaminomethyl)-(N-diphenylmethylen- 1-amino-2-phenylethyl)phosphinate (4)

A 1.53 N butyllithium solution (0.3 ml; 0.46 mmol) in hexane is added dropwise to a stirred solution of the ethyl phosphinate 3 (200 mg; 0.42 mmol) in THF (10 ml) at −78° C. under an atmosphere of argon. After 5 minutes benzyl bromide (0.06 ml; 0.51 mmol) is added dropwise to the deep-red reaction solution. After 2 hours the reaction solution is warmed to room temperature and after 15 hours diluted with ether. The solution is extracted with saturated aqueous ammonium chloride solution (2× 20 ml). The organic phase is dried over $Na_2SO_4$ and evaporated under reduced pressure. The monoalkylated phosphinate 4 (187 mg, 79% of theory) is obtained after purification on silica gel using column chromatography (ethyl acetate/heptane= 2/3).

$^1$H NMR (δ/ppm/)(200MHz, $CDCl_3$): 1.30 (3H, t, J 7 Hz, $CH_3$); 3.30 (dd, J 6 and 6 Hz, $CH_2Ph$); 3.90–4.15 (5H, m, CHN, $CH_2N$, $OCH_2$); 6.90–7.60 (25H, m, $H_{arom.}$)

MS (FAB, NBA, m/e): 571 (M+H$^+$), 284 (100%).

Example 6

Ethyl bis(N-diphenylmethylene-1-amino-2-phenylethyl)phosphinate (5)

A 1.53 N butyllithium solution (3.0 ml; 4.59 mmol) in hexane is added dropwise to a stirred solution of ethyl phosphinate 3 (1000 mg; 2.08 mmol) in THF (35 ml) at −78° C. under an atmosphere of argon. After 10 minutes benzyl bromide (1.00 ml; 8.42 mmol) is added dropwise to the deep-red reaction solution. After 70 hours stirring at −70° C. the reaction solution is diluted with ether and extracted with saturated aqueous ammonium chloride solution. The organic phase is dried over $Na_2SO_4$ and evaporated under reduced pressure. The bis-alkylated phosphinates 5 (1303 mg, 95% of theory) are obtained after purification on silica gel using column chromatography (ethyl acetate/heptane= 2/3).

$^1$H NMR (δ/ppm/) (200MHz, $CDCl_3$): 1.35 (3H, t, J 7 Hz); 3.00 (2H, m, $CH_2Ph$); 3.49 (2H, m, $CH_2Ph$); 4.15–4.30 (4H, m, $OCH_2$+2×CH—$CH_2Ph$); 6.90–7.60 (30H, m, $H_{arom}$);

MS (FAB, NBA, m/e): 661 (M+H$^+$); 284 (100%).

Example 7

Ethyl bis (N-diphenylmethylene-1-aminoethyl)phosphinate (6)

Analogously to Example 6, the bis-alkylated phosphinates 6 were prepared in a yield of 83% from the protected phosphinate 3 and methyl iodide.

MS (FAB, NBA, m/e): 509 (M+H$^+$).

Example 8

Ethyl bis(N-diphenylmethylene-1-amino-but-3-ynyl)phosphinate (7)

Analogously to Example 6, the bis-alkylated phosphinates 7 were prepared in a yield of 81% from the protected phosphinate 3 and propargyl bromide.

MS (FAB, NBA, m/e): 557 (M+H$^+$).

Example 9

Ethyl bis(N-diphenylmethylene-1-amino-4-phenyl-but-3-enyl)phosphinate (8)

Analogously to example 6, the bis-alkylated phosphinates 8 were prepared in a yield of 76% from the protected phosphinate 3 and cinnamyl bromide.

MS (FAB, NBA, m/e): 713 (M+H$^+$)

Example 10

Ethyl bis(N-diphenylmethylene-1-amino-3-bromobut-3-enyl)-phosphinate (9)

Analogously to Example 6, the bis-alkylated phosphinates 9 were prepared in a yield of 71% from the protected phosphinate 3 and 2,3-dibromopropene.

MS (FAB, NBA, m/e): 717, 719, 721 (M+H$^+$)

Example 11

Ethyl bis( 1-amino-2-phenylethyl)phosphinate hydrochloride (10)

Approximately 10% strength aqueous hydrochloric acid (30 ml) is added to a solution of the bis-alkylated phosphinate 5 (1161 mg; 1.76 mmol) in ether (30 ml) at room temperature with stirring. After 24 hours the organic phase is separated off and the aqueous phase is extracted with ethyl acetate (20 ml). The phosphinate hydrochloride 10 (690 mg, 97% of theory) is obtained after freeze-drying.

$^1$H NMR (δ/ppm/) (200 MHz, DMSO-$d_6$): 1.15 (3H, m, $CH_3$/diastereomeric mixture/); 3.05 (4H, m, $CH_2Ph$); 3.93 (1H, m, CH); 4.14–4.45 (3H, m, CH+$OCH_2$); 7.20–7.45 (10H, m, $H_{arom.}$); 8.70 (6H, bs, $NH_3$+);

MS (FAB, NBA, m/e): 333 (M+H+); 214; 120 (100%).

Example 12

Ethyl bis(1-aminoethyl)phosphinate hydrochloride (11)

Analogously to example 11, the phosphinate hydrochloride 11 is obtained in a yield of 95% from the protected phosphinate 6.

MS (FAB, NBA, m/e): 181 (M+H$^+$)

Example 13

Ethyl bis(1-aminobut-3-ynyl)phosphinate hydrochloride (12)

Analogously to Example 11, the phosphinate hydrochloride 12 is obtained in a yield of 93% from the protected phosphinate 7.

MS (FAB, NBA, m/e): 229 (M+H$^+$)

Example 14

Ethyl bis(1-amino-4-phenylbut-3-enyl)phosphinate hydrochloride (13)

Analogously to Example 11, the phosphinate hydrochloride 13 is obtained in a yield of 90% from the protected phosphinate 8.

MS (FAB, NBA, m/e): 385 (M+ H$^+$)

Example 15

Ethyl bis(1-amino-3-bromobut-3-enyl)phosphinate hydrochloride (14)

Analogously to Example 11, the phosphinate hydrochloride 14 is obtained in a yield of 82% from the protected phosphinate 9.

MS (FAB, NBA, m/e): 389, 391, 393 (M+ H$^+$)

Example 16

Bis (1-amino-2-phenylethyl)phosphinic acid hydrobromide (15)

A solution of the bis-alkylated phosphinate 5 (205 mg; 0.31 mmol) in 30% strength hydrogen bromide in glacial acetic acid (11 ml) is heated to a temperature of 55°– 65° C.

for 25 minutes. The phosphinic acid hydrobromide 15 (136 mg, 94% of theory) is obtained after evaporating the reaction solution under reduced pressure and repeated coevaporation with methanol and toluene.

$^1$H NMR (δ/ppm/) (200 MHz, DMSO-d$_6$): 3.03 (4H, m, CH$_2$Ph); 3.95 (1H, m, CH); 4.21 (1H, m, CH); 7.20–7.45 (10H, m, H$_{arom.}$); 8.72 ( 6H, bs, NH$_3$+ );

MS (FAB, NBA, m/e): 305 (M+H+); 120 (100%).

Example 17

Bis(1-amino-2-phenylethyl)phosphinic acid hydrobromide (15)

Analogously to Example 16, the phosphinic acid hydrobromide 15 is obtained in a yield of 92% from the phosphinate hydrochloride 10.

Example 18

Benzyl bis(N-tert-butoxycarbonyl-aminomethyl-phosphinate (16)

Analogously to Example 3, the benzyl phosphinate 16 (1.346 g, 55% of theory) was obtained from the phosphinic acid 1 (1.910 g; 5.90 mmol), benzyl alcohol (1.25 ml; 12.15mmol), isobutyl chloroformate (0.90 ml; 6.89mmol), triethylamine (1.00 ml; 7.19 mmol) and N,N-dimethylaminopyridine (70 mg; 0.57 mmol).

$^1$H NMR (δ/ppm/) (200 MHz, CDCl$_3$): 1.44 (18 H, s, (CH$_3$)$_3$C); 3.28 (2 H, dt, J 15 and 5 Hz, CH$_2$); 3.88 (2 H, m, CH$_2$); 5.13 (2 H, d, J 6 Hz, CH$_2$Ph); 5.25 (2 H, m, NH); 7.15– 7.45 (5 H, m, H$_{arom.}$);

MS (FAB, NBA, m/e): 415 (M+H$^+$)(100%); 359 (M-55).

Example 19

Methyl bis(N-tert-butoxycarbonyl-aminomethyl)phosphinate (17)

Analogously to Example 3, the phosphinate 17 (2.570 g, 29% of theory) was obtained from the phosphinic acid 1 (8.365 g; 28.82 mmol), methanol (5.50 ml; 135.78 mmol), isobutyl chloroformate (3.75 ml; 28.69 mmol), triethylamine (4.00 ml; 28.75mmol) and N,N-dimethylaminopyridine (330 mg; 2.70 mmol).

$^1$H NMR (δ/ppm/) (200 MHz, CDCl$_3$): 1.44 (18 H, s, (CH$_3$)$_3$C); 3.25 (2 H, dt, J 15 and 5 Hz, CH$_2$); 3.79 (3 H, d, g 10 Hz, OCH$_3$); 3.84 (2 H, m, CH$_2$); 5.46 (2 H, m, NH);

MS (FAB, NBA, m/e): 339 (M+H$^+$); 283 (M-55); 227 (100%).

Example 20

Methyl bis(aminomethyl)phosphinate hydrochloride (18)

The tert-butoxycarbonyl protective group of the methyl phosphinate 17 (2.470 g; 7.31 mmol) is removed using 3N. methanolic hydrochloric acid ( 50 ml ), by analogy with Example 4. The methyl phosphinate hydrochloride 18 is obtained (1.522 g, 99% of theory).

$^1$H NMR (δ/ppm/)(200 MHz, D$_2$O): 3.72 (2 H, d, J 10 Hz, CH$_2$); 3.73 (2 H, d, J 10 Hz, CH$_2$); 3.96 (3 H, d, J 10 Hz, OCH$_3$);

MS (FAB, NBA, m/e): 139 (M+H$^+$) (100%); 110.

Example 21

Ethyl bis(camphoriminemethyl)phosphinate (21)

A suspension of ethyl bis(aminomethyl)phosphinate hydrochloride (0.667 g; 2.96 mmol) and camphorimine (0.895 g; 5.93 mmol), see Example 21a), in methylene chloride (100 ml) is stirred intensively at room temperature.

After 65 hours, water is added to the reaction mixture. The aqueous phase is extracted with methylene chloride. The combined organic phase is dried and concentrated under reduced pressure. Following column-chromatographic purification on silica gel (ethyl ester/methanol, 95/5), the camphor compound 21 is obtained (0.969 g; 80% of theory).

$^1$H NMR (δ/ppm) (200 MHz, CDCl$_3$): 0.77 (6 H, s, CH$_3$); 0.91 (6 H, s, CH$_3$); 0.97 (6 H, s, CH$_3$); 1.16–2.06 (12 H, m, CH$_2$); 1.31 (3 H, t, J 6 Hz, CH$_2$CH$_3$); 2.47 (2 H, m, CH); 3.83 (4 H, m, PCH$_2$); 4.17 (2 H, dq, J 6 and 6 Hz, CH$_2$CH$_3$);
$^{31}$P (δ/ppm) (109 MHz, CDCl$_3$): 47.27;

MS (FAB, m/e): 421 (M+H$^+$) (100%); 164 (25%).

Example 21a (1R)-Camphorimine (20)

Sulphuric acid (1.1 ml; diluted with 20 ml of water) is added slowly, while stirring intensively, to a solution mixture composed of camphoroxime (19, see Example 21b) (3.65 g; 21.86 mmol) in ether (50 ml) and of sodium nitrite (3.65 g; 52.90 mmol) in water (20 ml). The reaction solution becomes claret-colored. After 15 minutes, the organic phase is separated off, dried and concentrated under reduced pressure. Under a nitrogen atmosphere, the solid oximenitrimine thus obtained changes color from yellow to turquoise, deliquescing in the process Ammonia is passed, at −15° C. into a suspension of the nitrimine in tetrahydrofuran (THF). After 30 minutes, the pale, amber-clear solution is concentrated under reduced pressure. The residue is taken up in methylene chloride. After filtering, the filtrate is concentrated under reduced pressure. The camphorimine (20) is obtained quantitatively as a crude product.

$^1$H NMR (δ/ppm)(200 MHz, CDCl$_3$): 0.80 (3 H, s, CH$_3$); 0.93 (3 H, s, CH$_3$); 0.95 (3 H, s, CH$_3$); 1.23–2.57 (7 H, m, CH$_2$+CH ); 5.81 (1 H, br, s, NH).

MS (CI, m/e: 152 (M+H$^+$)(100%), 95 (15%).

Example 21b (1R)-Camphoroxime (19)

Sodium hydroxide (15.03 g; 375.50 mmol) is added carefully to a solution, which is boiling under reflux, of (1R)(+)camphor (10.01 g; 65.86 mmol) and hydroxylamine hydrochloride (10.04 g; 144.46 mmol) in 150 ml of ethanol and 20 ml of water. After 7 hours, the reaction solution is cooled down, diluted with water and filtered. The filtrate is brought to a pH of 5–6 using acetic acid. After renewed filtration, the oxime 19 is obtained (3.81 g, 35% of theory) (m.p. 188°–20° C.).

$^1$H NMR (δ/ppm) (200 MHz, CDCl$_3$): 0.81 (3 H, s, CH$_3$); 0.92 (3 H, s, CH$_3$); 1.00 (3 H, s, CH$_3$); 1.15–2.12 (6 H, m, CH$_2$); 2.55 (1 H, dt, J 17 and 3 Hz, CH); 7.82 (1 H, s, OH).

Example 22

Ethyl bis(1-[camphorimine]-2-phenylethyl)phosphinate (22) ethyl(camphoriminemethyl)(1-[ camphorimine]-2-phenylethyl)phosphinate (23)

A 1.50 N solution of butyllithium (1.40 ml; 2.10mmol) is added dropwise, at −78° C. to a solution, which is stirred under an argon atmosphere, of the camphor compound 21 (0.320 g; 0.76 mmol) in abs. THF (30 ml). After 5 minutes, benzyl bromide (0.37 ml; 3.12 mmol) is added to this mixture. After 65 hours, a saturated aqueous solution of ammonium chloride is added to the reaction solution, which is diluted with ethyl acetate (EA). The aqueous phase is extracted with EA. The combined organic phase is dried and concentrated under reduced pressure. After chromatographic purification (EA/heptane, 9/1), two bisalkylated compounds 22 (43 mg, 9% of theory) and the monoalkylated compound 23 (131 mg, 34% of theory) are obtained.

22:

$^1$H NMR (δ/ppm)(200 MHz, CDCl$_3$): 0.66–1.02 (18 H, m, CH$_3$); 1.20–2.46 (17 H, m, CH$_2$+CH+CH$_2$CH$_2$CH$_3$); 2.88–3.58 (4 H, m, CH$_2$Ph); 3.82–4.35 (4 H, m, PCH+ CH$_2$CH$_3$); 7.10–7.28 (10 H, m, H$_{arom.}$);

$^{31}$P (δ/ppm)(109 MHz, CDCl$_3$); 48.55; 48.84; MS (FAB, m/e): 601 (M+H$^+$) (100%), 567 (15%), 254 (82%).

23:

$^1$H NMR (δ/ppm)(200 MHz, CDCl$_3$): 0.68 (3 H, s, CH$_3$); 0.78 (3 H, s, CH$_3$); 0.82 (3 H, s, CH$_3$); 0.92 (3 H, s, CH$_3$); 0.94 (3 H, s, CH$_3$); 0.97 (3 H, s, CH$_3$); 1.30–2.08 (15 H, m, CH$_2$+CH$_2$CH$_3$); 2.27 (1 H, dd, J 16 Hz, CH); 2.46 (1 H, dd, J 16 Hz, CH); 3.08 (1H, m α-CH$_2$OH); 3.34 (1 H, m, β-CH 2Ph); 3.63–4.35 (5 H, m, PCH$_2$+PCH+CH$_2$CH$_3$); 7.13–7.30 (5 H, m, H$_{arom.}$);

$^{31}$P (δ/ppm)(109 MHz, CDCl$_3$); 48.44; 48.95;

MS (FAB, m/e): 601 (M+H$^+$) (100%), 360 (5%), 254 (38%).

We claim:

1. A process for the preparation of α- or α,α'-substituted derivatives of the bis(aminomethyl)phosphinic acid of the formula I and their acid or basic salts

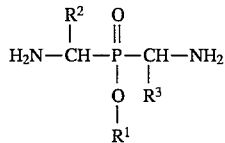
(I)

in which R$^1$ is R$^6$=C$_1$–C$_{18}$ alkyl, C$_2$–C$_{18}$ alkenyl, C$_2$–C$_{18}$ alkynyl, C$_6$–C$_{12}$ aryl or C$_7$–C$_{20}$ arylalkyl and aryl or arylalkyl may be mono- or polysubstituted by fluorine, chlorine, bromine, NO$_2$, CN, OH, COOH, C$_1$–C$_6$ alkyl, C$_1$–C$_6$ alkoxy, C(O)—O—(C$_1$–C$_6$) alkyl, C(O)—(C$_1$–C$_6$) alkyl or O—C(O)—(C$_1$–C$_6$) alkyl and R$^1$ is also hydrogen or basic or acid salt radicals of α-or α,α'-substituted derivatives of the bis(aminomethyl)phosphinic acid, R$^2$ and R$^3$ are identical or different and are, independently of each other, hydrogen, C$_1$–C$_{18}$ alkyl, C$_2$–C$_{18}$ alkenyl, C$_2$–C$_{18}$ alkynyl, C$_6$–C$_{12}$ aryl or C$_7$–C$_{22}$ arylalkyl, where alkyl, alkenyl or alkynyl may each be mono- or polysubstituted by fluorine, chlorine, bromine, NO$_2$, NH$_2$, CN, OH, COOH, C(O)—O—(C$_1$–C$_6$) alkyl, C(O)—(C$_1$–C$_6$) alkyl, O—C(O)—(C$_1$–C$_6$) alkyl or C$_1$–C$_6$ alkoxy and aryl or arylalkyl may be mono- or polysubstituted by fluorine, chlorine, bromine, NO$_2$, CN, OH, COOH, C$_1$–C$_6$ alkyl, C$_1$–C$_6$ alkoxy, C(O)—O—(C$_1$–C$_6$) alkyl, C(O)—(C$_1$–C$_2$) alkyl or O—C(O)— (C$_1$–C$_6$) alkyl, with the proviso that if R$^2$= hydrogen and R$^3$ has the abovementioned meaning, R$^3$ must not also be hydrogen, and vice versa, which comprises a) esterifying bis(aminomethyl)phosphinic acid, after introducing amino protective groups, with a compound of the formula R$^6$—OH in which R$^6$ has the meaning mentioned under R$^1$, or b) initially esterifying bis(chloromethyl)phosphinyl chloride with a compound of the formula R$^6$—OH, reacting the compound thus obtained with benzylamine to give the bis(N-benzylaminomethyl) phosphinate, then, after removing the amino protective groups from the compounds obtained by a) or b), reacting the bis(aminomethyl)phosphinate of the formula IV

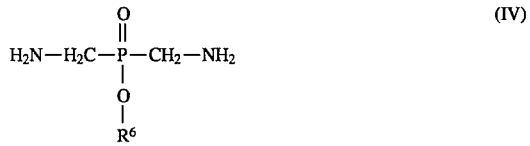
(IV)

in which R$^6$ is as defined above, with a compound of the formula VI

(VI)

or a compound of the formula VII

(VII)

in which R$^7$ and R$^8$ are identical or different and are hydrogen, C$_1$–C$_{20}$ alkyl, C$_2$–C$_{20}$ alkenyl, C$_2$–C$_{20}$ alkynyl or C$_6$–C$_{12}$ aryl or R$^7$ and R$^8$ together form a ring system, under conditions in which water is removed, to give a compound of the formula V

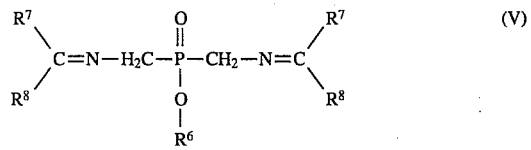
(V)

in which R$^6$, R$^7$ and R$^8$ have the abovementioned meaning, e$_1$) converting the compound of the formula V to a compound of the formula VIII

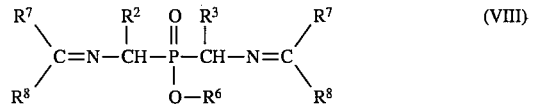
(VIII)

in which R$^2$=R$^3$ and R$^3$, R$^6$, R$^7$ and R$^8$ have the abovementioned meaning, except for R$^3$= hydrogen, after reaction with 2–3 equivalents of base, with 2–5 equivalents of a compound of the formula R$^3$—X, in which R$^3$ has the abovementioned meaning, except for hydrogen, and X is a leaving group, or e$_2$) proceeding in an analogous manner to e$_1$), but using 1 to 1.2 equivalents of base and 1 to 1.2 equivalents of R$^3$—X, obtaining a compound of the formula VIII in which R$^2$ is hydrogen and R$^3$, R$^6$, R$^7$ and R$^8$ have the abovementioned meaning, except for R$^3$ = hydrogen, optionally e$_3$) reacting the compound of the formula VIII obtained in e$_2$), after reaction with a further 1 to 1.2 equivalents of a base, with 1 to 1.2 equivalents of a compound of the formula R$^2$—X in which R$^2$ and X have the abovementioned meaning, except for R$^2$= hydrogen, to give a compound of the formula VIII in which R$^2$, R$^3$, R$^6$, R$^7$ and R$^8$ have the abovementioned meaning, except for R$^2$ and R$^3$= hydrogen, or f$_1$) reacting the compound of the formula V with a catalyst of the formula R$^9$R$^{10}$R$^{11}$R$^{12}$NZ 2 to 3 equivalents of a compound of the formula R$^3$—X and 2–25 equivalents of an alkali metal hydroxide or alkaline earth metal hydroxide, where N is nitrogen or phosphorus, Z is an anion of an inorganic salt, , $R^9$, $R^{10}$, $R^{11}$ and $R^{12}$ are identical or different and, independently of each other, are $C_6$–$C_{10}$ alkyl, $C_2$–$C_{20}$ alkenyl, $C_2$–$C_{20}$ alkynyl, $C_6$–$C_{12}$ aryl or $C_7$–$C_{20}$ arylalkyl and $R^3$ and X are as defined in $e_1$), in the presence of a water-immiscible solvent with water, to give a compound of the formula VIII in which $R^2$=$R^3$ and $R^3$, $R^6$, $R^7$ and $R^8$ have the abovementioned meaning, except for $R^3$= hydrogen, or $f_2$) proceeding in an analogous manner to $f_1$), but using 2–10 equivalents of an alkali metal or alkaline earth metal hydroxide and 1 to 1.2 equivalents of $R^3$—X obtaining a compound of the formula VIII in which $R^2$ is hydrogen and $R^3$, $R^6$, $R^7$ and $R^8$ have the abovementioned meaning, except for $R^3$= hydrogen, optionally $f_3$) reacting the compound of the formula VIII obtained by $f_2$), under the conditions mentioned in $f_1$), with $R^2$—X instead of $R^3$—X to give a compound of the formula VIII in which $R^2$, $R^3$, $R^6$, $R^7$ and $R^8$ have the abovementioned meaning, except for $R^2$ and $R^3$=hydrogen, using, however, 2 to 10 equivalents of the alkali metal or alkaline earth metal hydroxide and 1 to 1.2 equivalents of $R^2$—X, or g) proceeding in an analogous manner to $f_1$)–$f_3$), but using no solvent, and with methyltrioctylammonium chloride instead of $R^9R^{10}R^{11}R^{12}NZ$ obtaining a compound of the formula VIII with the meanings mentioned in $f_1$)–$f_3$), h) reacting the compound of the formula VIII obtained by e), f) or g) with 5–15% strength aqueous HCl or HBr to give a compound of the formula I, in which $R^1$ is $R^6$ and $R^2$ and $R^3$ have the meaning mentioned in e), f) or g), or i) reacting the compound of the formula VIII obtained by e), f) or g) or optionally the compound of the formula I obtained by h) with 30% strength HBr or HCl in glacial acetic acid to give a compound of the formula I in which $R^2$ and $R^3$ have the meaning mentioned in e), f) or g) and $R^1$ is defined as above, $R^1$, however, not being $R^6$.

2. A process according to claim 1, wherein $R^1$ is selected from the group consisting of hydrogen, $C_1$–$C_4$ alkyl, $C_2$–$C_4$ alkenyl, phenyl, benzyl, Li$^+$, Na$^+$, K$^+$, Mg$^{2+}$, NH$_4^+$, and HN(C$_2$H$_5$)$_3^+$.

3. A process according to claim 1, wherein $R^1$ is selected from the group consisting of hydrogen and $C_1$–$C_4$ alkyl.

4. A process according to claim 1, wherein $R^2$ and $R^3$ are identical or different and are selected from the group consisting of $C_1$–$C_6$ alkyl, $C_2$–$C_6$ alkenyl, $C_2$–$C_6$ alkynyl, $C_6$–$C_{12}$ aryl, and $C_7$–$C_{13}$ arylalkyl.

5. A process according to claim 4, wherein said aryl or arylalkyl is mono- or polysubstituted with chlorine, bromine, —CN, or O—$C_1$–$C_3$ alkyl.

6. A process according to claim 1, wherein $R^2$ and $R^3$ are identical or different and are selected from the group consisting of $C_1$–$C_6$ alkyl, $C_2$–$C_6$ alkenyl, $C_2$–$C_6$ alkynyl, and benzyl.

7. A process according to claim 1, wherein said acid salts are selected from the group consisting of hydrochlorides, hydrobromides, and hydrogen sulfates.

* * * * *

UNITED STATES PATENT AND TRADEMARK OFFICE
CERTIFICATE OF CORRECTION

PATENT NO. : 5,510,504
DATED : April 23, 1996
INVENTOR(S) : Anuschirwan PEYMAN et al It is certified that error appears in the above-indentified patent and that said Letters Patent is hereby corrected as shown below:

Claim 1, Column 13, Line 54, "$C(O)-(C_1-C_2)$ should read -- $C(O)-(C_1-C_6)$--.

Claim 1, Column 13, Line 61, after "$R^6$-OH", insert --,--;

Claim 1, Column 14, Line 63, after "$R^9R^{10}R^{11}R^{12}NZ$" insert --,--;

Claim 1, Column 14, Line 67, after "salt,", delete ",";

Claim 1, Column 15, Line 2, "$C_6-C_{10}$" should read --$C_1-C_{10}$--;

Claim 1, Column 15, Line 19, after "$R^3$-X", insert --,--;

UNITED STATES PATENT AND TRADEMARK OFFICE
CERTIFICATE OF CORRECTION

PATENT NO. : 5,510,504
DATED : April 23, 1996
INVENTOR(S) : Anuschirwan PEYMAN et al It is certified that error appears in the above-indentified patent and that said Letters Patent is hereby corrected as shown below:

Claim 1, Column 15, Line 27, after "$R^9R^{10}R^{11}R^{12}NZ$", insert --,--.

Signed and Sealed this

Thirty-first Day of December, 1996

Attest:

BRUCE LEHMAN

*Attesting Officer*     *Commissioner of Patents and Trademarks*